United States Patent
Horikoshi et al.

(10) Patent No.: US 9,133,151 B2
(45) Date of Patent: Sep. 15, 2015

(54) METHOD FOR PRODUCING BIS($\beta$-EPDXYPROPYL)SULFIDE AND BIS($\beta$-EPDXYPROPYL)POLYSULFIDE

(71) Applicant: MITSUBISHI GAS CHEMICAL COMPANY, INC., Tokyo (JP)

(72) Inventors: Hiroshi Horikoshi, Tokyo (JP); Motoharu Takeuchi, Ibaraki (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/402,442

(22) PCT Filed: Jun. 21, 2013

(86) PCT No.: PCT/JP2013/067032
§ 371 (c)(1),
(2) Date: Nov. 20, 2014

(87) PCT Pub. No.: WO2014/002876
PCT Pub. Date: Jan. 3, 2014

(65) Prior Publication Data
US 2015/0158836 A1    Jun. 11, 2015

(30) Foreign Application Priority Data

Jun. 26, 2012 (JP) ................. 2012-143171
Aug. 20, 2012 (JP) ................. 2012-181523
Aug. 20, 2012 (JP) ................. 2012-181524

(51) Int. Cl.
*C07D 301/27* (2006.01)
*C07D 303/34* (2006.01)

(52) U.S. Cl.
CPC .................... *C07D 303/34* (2013.01)

(58) Field of Classification Search
CPC ..................... C07D 301/27; C07D 303/34
USPC ........................................ 549/514
See application file for complete search history.

(56) References Cited

U.S. PATENT DOCUMENTS 5,807,975 A     9/1998 Amagai et al.
2005/0124783 A1  6/2005 Morijiri et al.

FOREIGN PATENT DOCUMENTS

| JP | 9-71580 | 3/1997 |
| JP | 9-110979 | 4/1997 |
| JP | 11-180977 | 7/1999 |
| JP | 11-322930 | 11/1999 |
| JP | 2000-143651 | 5/2000 |
| JP | 2003-48883 | 2/2003 |
| JP | 2003-335859 | 11/2003 |
| WO | 2009/066687 | 5/2009 |

OTHER PUBLICATIONS

U.S. Appl. No. 14/414,585 to Hiroyuki Okada et al., filed Jan. 13, 2015.
Search report from PCT/JP2013/067032, mail date is Sep. 10, 2013.

*Primary Examiner* — T. Victor Oh
(74) *Attorney, Agent, or Firm* — Greenblum & Bernstein, P.L.C.

(57) ABSTRACT

According to the present invention, a method for producing bis($\beta$-epoxypropyl)sulfide or bis($\beta$-epoxypropyl)polysulfide can be provided, which is characterized by comprising adding a metal compound selected from the group consisting of a metal hydrosulfide, a metal sulfide and a metal polysulfide to an epihalohydrin at $-5$ to $30°$ C. in such a manner that the molar ratio of the epihalohydrin to the metal compound becomes 5 to 20 to thereby cause the reaction of the epihalohydrin with the metal compound. In a preferred embodiment, the epihalohydrin is epichlorohydrin, the metal hydrosulfide is sodium hydrosulfide or potassium hydrosulfide, the metal sulfide is sodium sulfide or potassium sulfide, and the metal polysulfide is sodium polysulfide or potassium polysulfide.

6 Claims, No Drawings

METHOD FOR PRODUCING BIS(β-EPDXYPROPYL)SULFIDE AND BIS(β-EPDXYPROPYL)POLYSULFIDE

TECHNICAL FIELD

The present invention relates to a sulfur-containing epoxy compound and a method for producing the same. The present invention particularly relates to a sulfur-containing epoxy compound, which may be a raw material of an episulfide compound suitably used for optical materials for a plastic lens, a prism, an optical fiber, an information recording substrate, a filter or the like, in particular for a plastic lens, and a method for producing the same.

BACKGROUND ART

Plastic materials are lightweight, highly tough and easy to be dyed, and therefore are widely used recently for various types of optical materials, particularly eyeglass lenses. Optical materials, particularly eyeglass lenses, are specifically required to have, as physical properties, low specific gravity, high transparency and low yellowness, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number is decreased. Therefore, it has been studied to improve both of the refractive index and the Abbe number. Among methods which have been proposed, the most representative method is a method using an episulfide compound as described in Patent Document 1.

This episulfide compound is obtained by producing a sulfur-containing epoxy compound in which a sulfur atom at the epithio moiety is replaced with an oxygen atom and then sulfidating the compound. As methods for producing a sulfur-containing epoxy compound, the production methods described in Patent Documents 1-3 have been proposed, and the yield and transparency of resin obtained by curing an episulfide compound obtained by sulfidation have been improved.

However, in these production methods, hydrogen sulfide is used as the main raw material and it is difficult to handle it. Patent Document 1 shows a production method in which hydrogen sulfide is not used. However, according to the method, the yield was low, and since a large amount of oligomer was produced, it was difficult to perform purification by distillation after that.

Accordingly, the development of a method for producing a sulfur-containing epoxy compound, wherein hydrogen sulfide is not used and the production of oligomer is suppressed, has been desired.

Further, it is necessary to cause a reaction with a basic compound after the reaction, and therefore a two-stage reaction is carried out. Accordingly, the development of a method for producing a sulfur-containing epoxy compound in good yield in one step, wherein hydrogen sulfide is not used and the production of oligomer is suppressed, has been also desired.

In addition, as a technique of increasing the refractive index, the episulfide compound having disulfide shown in Patent Document 4 has been proposed. This episulfide compound is obtained by producing a sulfur-containing epoxy compound in which a sulfur atom at the epithio moiety is replaced with an oxygen atom and then sulfidating the compound.

However, in this production method, hydrogen sulfide is used as the main raw material and it may be difficult to handle it. Moreover, it is necessary to synthesize a disulfide bond using halogen after the reaction, and the reaction is complicated.

Furthermore, when trying to further increase the refractive index, disulfide is the limit of the technique shown in Patent Document 4, and it is impossible to produce an epoxy compound having polysulfide that is tri- or higher sulfide. Therefore, a method for producing an epoxy compound having polysulfide has been desired.

Accordingly, the development of a method for producing an epoxy compound having polysulfide, wherein hydrogen sulfide is not used, has been also desired.

PRIOR ART DOCUMENTS

Patent Documents

Patent Document 1: Japanese Laid-Open Patent Publication No. H09-71580
Patent Document 2: Japanese Laid-Open Patent Publication No. 2000-143651
Patent Document 3: Japanese Laid-Open Patent Publication No. 2003-48883
Patent Document 4: Japanese Laid-Open Patent Publication No. H11-322930

SUMMARY OF THE INVENTION

Problems to be Solved by the Invention

The problem to be solved by the present invention is to provide a method for producing bis(β-epoxypropyl)sulfide that is a sulfur-containing epoxy compound in good yield, wherein hydrogen sulfide is not used and the production of oligomer is suppressed. Moreover, another problem to be solved by the present invention is to provide a method for producing bis(β-epoxypropyl)sulfide that is a sulfur-containing epoxy compound in good yield in one step, wherein hydrogen sulfide is not used and the production of oligomer is suppressed. Furthermore, another problem to be solved by the present invention is to provide a method for producing bis(β-epoxypropyl)polysulfide that is an epoxy compound having polysulfide, wherein hydrogen sulfide is not used.

Means for Solving the Problems

Under such circumstances, the present inventors diligently made researches, and found that, by using an epihalohydrin, a metal hydrosulfide and a basic compound to cause a reaction under specific conditions, bis(β-epoxypropyl)sulfide that is a sulfur-containing epoxy compound can be obtained in good yield, wherein hydrogen sulfide is not used and the production of oligomer is suppressed. The present inventors further found that, by reacting an epihalohydrin with a metal sulfide under specific conditions, bis(β-epoxypropyl)sulfide that is a sulfur-containing epoxy compound can be obtained in good yield in one step, wherein hydrogen sulfide is not used and the production of oligomer is suppressed. The present inventors further found that, by means of the production method in which an epihalohydrin is reacted with a metal polysulfide to obtain a sulfur-containing epoxy compound, an epoxy compound having polysulfide can be obtained, wherein hydrogen sulfide is not used. Specifically, the present invention is as follows:

<1> A method for producing bis(β-epoxypropyl)sulfide or bis(β-epoxypropyl)polysulfide, which comprises adding a metal compound selected from the group consisting of a metal hydrosulfide, a metal sulfide and a metal polysulfide to an epihalohydrin at −5 to 30° C. in such a manner that the molar ratio of the epihalohydrin to the metal compound (i.e., epihalohydrin/metal compound) becomes 5 to 20 to thereby cause the reaction of the epihalohydrin with the metal compound.

<2> The method according to item <1>, wherein the epihalohydrin is epichlorohydrin and the metal hydrosulfide is sodium hydrosulfide or potassium hydrosulfide.

<3> The method according to item <1>, wherein the epihalohydrin is epichlorohydrin and the metal sulfide is sodium sulfide or potassium sulfide.

<4> The method according to item <1>, wherein the epihalohydrin is epichlorohydrin and the metal polysulfide is sodium polysulfide or potassium polysulfide.

<5> The method according to item <1> or <2>, wherein: the metal hydrosulfide is added to the epihalohydrin at −5 to 30° C. in such a manner that the molar ratio of the epihalohydrin to the metal hydrosulfide becomes 5 to 20 to thereby cause the reaction of the epihalohydrin with the metal hydrosulfide; and then a basic compound is further added thereto in such a manner that the molar ratio of the basic compound to the metal hydrosulfide becomes 1.0 to 3.5 to thereby cause the reaction of the basic compound therewith at −5 to 30° C.

Advantageous Effect of the Invention

According to the production method of the present invention, it is possible to produce bis(β-epoxypropyl)sulfide that is a sulfur-containing epoxy compound, wherein hydrogen sulfide is not used and the production of oligomer is suppressed, which was impossible by means of the conventional production methods. Since hydrogen sulfide is not used and the production of oligomer is suppressed, bis(β-epoxypropyl) sulfide that is the sulfur-containing epoxy compound can be easily obtained in good yield, and it is very meaningful. Moreover, according to the production method of the present invention, it is possible to produce bis(β-epoxypropyl)sulfide that is a sulfur-containing epoxy compound in good yield in one step, wherein hydrogen sulfide is not used and the production of oligomer is suppressed, which was impossible by means of the conventional production methods. Since hydrogen sulfide is not used, the process is carried out in one step and the production of oligomer is suppressed, bis(β-epoxypropyl)sulfide that is the sulfur-containing epoxy compound can be easily obtained in good yield, and it is very meaningful. Furthermore, according to the production method of the present invention, it is possible to produce an epoxy compound having polysulfide, wherein hydrogen sulfide is not used, which was impossible by means of the conventional production methods.

EMBODIMENTS FOR CARRYING OUT THE INVENTION

The present invention is a method for producing bis(β-epoxypropyl)sulfide or bis(β-epoxypropyl)polysulfide, wherein a metal compound selected from the group consisting of a metal hydrosulfide, a metal sulfide and a metal polysulfide is added to an epihalohydrin at −5 to 30° C. in such a manner that the molar ratio of the epihalohydrin to the metal compound becomes 5 to 20 to thereby cause the reaction of the epihalohydrin with the metal compound.

First Preferred Embodiment

The first preferred embodiment of the present invention is a production method, wherein: the metal hydrosulfide is added to the epihalohydrin at −5 to 30° C. in such a manner that the molar ratio of the epihalohydrin to the metal hydrosulfide becomes 5 to 20 to thereby cause the reaction of the epihalohydrin with the metal hydrosulfide; and then a basic compound is further added thereto in such a manner that the molar ratio of the basic compound to the metal hydrosulfide becomes 1.0 to 3.5 to thereby cause the reaction of the basic compound therewith at −5 to 30° C. According to the first preferred embodiment of the present invention, a sulfur-containing epoxy compound represented by formula (1) below (bis(β-epoxypropyl)sulfide) is obtained.

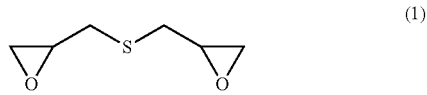

(1)

The oligomer, the generation of which is to be suppressed in the first preferred embodiment of the present invention, is a compound obtained by allowing a reaction intermediate to be polymerized, and the structure represented by formula (2) below is a typical structure thereof. To quantitate the compound having the structure of formula (2) provides an indication of whether or not it is possible to carry out the suppression of the production of the oligomer, which is the objective of the present invention.

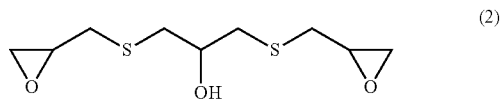 [SMILES: OC(CSCC1CO1)CSCC1CO1]

(2)

The epihalohydrin to be used in the first preferred embodiment of the present invention includes every compound, but is preferably epichlorohydrin, which is easily available. The metal hydrosulfide to be used in the first preferred embodiment of the present invention includes every compound, but is preferably sodium hydrosulfide or potassium hydrosulfide, which is easily available, and more preferably sodium hydrosulfide.

The reaction of the epihalohydrin with the metal hydrosulfide, which is the first reaction stage of the first preferred embodiment of the present invention, is as described below.

The metal hydrosulfide is added to the epihalohydrin to cause the reaction. At this time, the metal hydrosulfide is added in such a manner that the molar ratio of the epihalohydrin to the metal hydrosulfide becomes 5 to 20. The molar ratio is preferably 5 to 15, and more preferably 5 to 10. Note that the molar ratio as used herein means a molar ratio of the feed amount of the epihalohydrin to the final amount of the metal hydrosulfide to be added, but not an actual molar ratio in the reaction system.

When the molar ratio of the epihalohydrin to the metal hydrosulfide is less than 5, the production of the compound of formula (2) is increased to cause reduction in the yield. Moreover, when purification by distillation is performed after that, the compound of formula (2) remains as a still residue, and therefore it becomes difficult to carry out the treatment.

Meanwhile, when the molar ratio of the epihalohydrin to the metal hydrosulfide is more than 20, since a large excess amount of the epihalohydrin is used, it is economically undesirable.

Regarding the addition of the metal hydrosulfide to the epihalohydrin, gradual addition is preferred because the amount of the compound of formula (2) produced in the case of gradual addition is smaller than the amount in the case of addition at a time.

The solvent is not particularly required to be used as long as the epihalohydrin reacts with the metal hydrosulfide, but it is preferred to use a solvent. When using a solvent, water, alcohols, ethers, aliphatic hydrocarbons, aromatic hydrocarbons and halogenated hydrocarbons are preferred, water and alcohols are more preferred, water and methanol are even more preferred, and methanol is most preferred. These solvents may be used solely or in combination.

It is preferred to use the solvent in order to dissolve the metal hydrosulfide. In addition, it is preferred to react the epihalohydrin with the metal hydrosulfide dissolved in the solvent, and it is more preferred to dropwisely add the metal hydrosulfide dissolved in the solvent to the epihalohydrin.

The reaction temperature is −5 to 30° C., preferably 0 to 20° C., and most preferably 5 to 15° C. When the reaction temperature is lower than −5° C., the reaction rate is reduced and it is economically undesirable. When the reaction temperature is higher than 30° C., the amount of the compound of formula (2) is increased, and it is undesirable.

Note that it is preferred to carry out stirring for 1 minute to 10 hours after the completion of the addition of the metal hydrosulfide in order to complete the first reaction stage. The time is more preferably 5 minutes to 5 hours, and even more preferably 10 minutes to 3 hours.

After the epihalohydrin is reacted with the metal hydrosulfide, as the second reaction stage, a basic compound is added to and reacted with the reaction product obtained by the first reaction stage.

The basic compound to be used in the first preferred embodiment of the present invention is not particularly limited and any basic compound may be used, but it is preferably amine, an alkali metal or an alkaline-earth metal salt, and more preferably an alkali metal or an alkaline-earth metal salt. Preferred specific examples thereof include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Among them, sodium hydroxide, potassium hydroxide, magnesium hydroxide and calcium hydroxide are preferred, and sodium hydroxide and potassium hydroxide are more preferred.

The basic compound is added in such a manner that the molar ratio of the basic compound to the metal hydrosulfide becomes 1.0 to 3.5. The molar ratio is more preferably 1.2 to 3.0, and even more preferably 1.5 to 3.0. Note that the molar ratio as used herein means a molar ratio of the amount of the basic compound to be added to the amount of the metal hydrosulfide to be added at the first reaction stage, but not an actual molar ratio in the reaction system.

When the molar ratio of the basic compound to the metal hydrosulfide is less than 1.0, the epoxy compound is not sufficiently produced and the yield is reduced. When the molar ratio of the basic compound to the metal hydrosulfide is more than 3.5, the number of times of the washing operation for removing excess bases is increased and it is economically undesirable. Moreover, as the number of times of washing is increased, the yield is reduced.

Regarding the addition of the basic compound to the reaction product obtained by the first reaction stage, gradual addition is more preferred compared to addition at a time in terms of controlling the reaction.

The solvent is not particularly required to be used as long as the basic compound reacts with the reaction product of the epihalohydrin and the metal hydrosulfide, but it is preferred to use a solvent. When using a solvent, water, alcohols, ethers, aliphatic hydrocarbons, aromatic hydrocarbons and halogenated hydrocarbons are preferred, water and alcohols are more preferred, water and methanol are even more preferred, and water is most preferred. These solvents may be used solely or in combination.

It is preferred to use the solvent in order to dissolve the basic compound. In addition, it is preferred to dissolve the basic compound in the solvent, followed by reacting it with the reaction product of the epihalohydrin and the metal hydrosulfide, and it is more preferred to dissolve the basic compound in the solvent, followed by dropwisely adding it to the reaction product of the epihalohydrin and the metal hydrosulfide.

The reaction temperature at the second reaction stage is −5 to 30° C., preferably 0 to 20° C., and most preferably 5 to 15° C. When the reaction temperature is lower than −5° C., the reaction rate is reduced and it is economically undesirable. When the reaction temperature is higher than 30° C., the amount of the compound of formula (2) is increased, and it is undesirable.

Note that it is preferred to carry out stirring for 1 minute to 10 hours after the completion of adding dropwisely in order to complete the second reaction stage. The time is more preferably 5 minutes to 5 hours, and even more preferably 10 minutes to 3 hours.

After the completion of the reaction, it is preferred to add an organic solvent thereto to extract bis(β-epoxypropyl)sulfide that is the sulfur-containing epoxy compound of interest. As the organic solvent, hydrocarbons, ethers, aliphatic hydrocarbons, aromatic hydrocarbons and halogenated hydrocarbons are preferred, and aromatic hydrocarbons and halogenated hydrocarbons are more preferred. Preferred specific examples thereof include toluene, benzene, xylene, dichloromethane and chloroform, and toluene is most preferred. Further, the obtained organic layer is preferably washed with water in order to remove the basic compound. Washing with water is carried out more preferably until the pH of water for washing becomes 10 or less, and even more preferably until the pH of water for washing becomes 9 or less.

The solvent is distilled away from the thus obtained organic layer, thereby obtaining bis(β-epoxypropyl)sulfide that is the sulfur-containing epoxy compound of interest.

According to the production method of the first preferred embodiment of the present invention, it is possible to produce a sulfur-containing epoxy compound represented by formula (1), wherein hydrogen sulfide is not used and the production of oligomer is suppressed, which was impossible by means of the conventional production methods. Since hydrogen sulfide is not used and the production of the compound represented by formula (2) is suppressed, bis(β-epoxypropyl)sulfide that is the sulfur-containing epoxy compound can be easily obtained in good yield.

Second Preferred Embodiment

The second preferred embodiment of the present invention relates to a method for producing a sulfur-containing epoxy compound represented by formula (1) below (bis(β-epoxypropyl)sulfide), wherein a metal sulfide is added to the epihalohydrin at −5 to 30° C. in such a manner that the molar ratio of the epihalohydrin to the metal sulfide becomes 5 to 20 to cause the reaction.

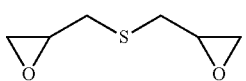

(1)

The oligomer, the generation of which is to be suppressed in the second preferred embodiment of the present invention, is a compound obtained by allowing a reaction intermediate to be polymerized, and the structure represented by formula (2) below is a typical structure thereof. To quantitate the compound having the structure of formula (2) provides an indication of whether or not it is possible to carry out the suppression of the production of the oligomer, which is the objective of the present invention.

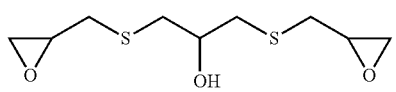

(2)

The epihalohydrin to be used in the second preferred embodiment of the present invention includes every compound, but is preferably epichlorohydrin, which is easily available. The metal sulfide to be used in the second preferred embodiment of the present invention includes every compound, but is preferably sodium sulfide or potassium sulfide, which is easily available, and more preferably sodium sulfide.

The reaction of the epihalohydrin with the metal sulfide is as described below.

The metal sulfide is added to the epihalohydrin to cause the reaction. At this time, the metal sulfide is added in such a manner that the molar ratio of the epihalohydrin to the metal sulfide becomes 5 to 20. The molar ratio is preferably 5 to 15, and more preferably 5 to 10. Note that the molar ratio as used herein means a molar ratio of the feed amount of the epihalohydrin to the final amount of the metal sulfide to be added, but not an actual molar ratio in the reaction system.

When the molar ratio of the epihalohydrin to the metal sulfide is less than 5, the production of the compound of formula (2) is increased to cause reduction in the yield. Moreover, when purification by distillation is performed after that, the compound of formula (2) remains as a still residue, and therefore it becomes difficult to carry out the treatment.

Meanwhile, when the molar ratio of the epihalohydrin to the metal sulfide is more than 20, since a large excess amount of the epihalohydrin is used, it is economically undesirable.

Regarding the addition of the metal sulfide to the epihalohydrin, gradual addition is preferred because the amount of the compound of formula (2) produced in the case of gradual addition is smaller than the amount in the case of addition at a time.

The solvent is not particularly required to be used as long as the epihalohydrin reacts with the metal sulfide, but it is preferred to use a solvent. When using a solvent, water, alcohols, ethers, aliphatic hydrocarbons, aromatic hydrocarbons and halogenated hydrocarbons are preferred, water and alcohols are more preferred, water and methanol are even more preferred, and water is most preferred. These solvents may be used solely or in combination.

It is preferred to use the solvent in order to dissolve the metal sulfide. In addition, it is preferred to react the epihalohydrin with the metal sulfide dissolved in the solvent, and it is more preferred to dropwisely add the metal sulfide dissolved in the solvent to the epihalohydrin.

The reaction temperature is −5 to 30° C., preferably 0 to 20° C., and most preferably 5 to 15° C. When the reaction temperature is lower than −5° C., the reaction rate is reduced and it is economically undesirable. When the reaction temperature is higher than 30° C., the amount of the compound of formula (2) is increased, and it is undesirable.

Note that it is preferred to carry out stirring for 1 minute to 10 hours after the completion of the addition of the metal sulfide in order to complete the reaction. The time is more preferably 5 minutes to 5 hours, and even more preferably 10 minutes to 3 hours.

After the epihalohydrin is reacted with the metal sulfide, a basic compound may be further reacted therewith in order to complete the reaction.

The basic compound is not particularly limited and any basic compound may be used, but it is preferably amine, an alkali metal or an alkaline-earth metal salt, and more preferably an alkali metal or an alkaline-earth metal salt. Preferred specific examples thereof include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Among them, sodium hydroxide, potassium hydroxide, magnesium hydroxide and calcium hydroxide are preferred, and sodium hydroxide and potassium hydroxide are more preferred.

When adding the basic compound, any amount of the basic compound may be added, but in view of economic efficiency, the amount of the basic compound is 1 equivalent or less, and more preferably 0.5 equivalent or less relative to the metal sulfide.

The solvent to be used at this time is not particularly limited, but water, alcohols, ethers, aliphatic hydrocarbons, aromatic hydrocarbons and halogenated hydrocarbons are preferred, water and alcohols are more preferred, water and methanol are even more preferred, and water is most preferred. These solvents may be used solely or in combination. Further, it is preferred to dissolve the basic compound in the solvent, followed by dropwisely adding it to the reaction product of the epihalohydrin and the metal sulfide.

The reaction temperature is −5 to 30° C., preferably 0 to 20° C., and most preferably 5 to 15° C. When the reaction temperature is lower than −5° C., the reaction rate is reduced and it is economically undesirable. When the reaction temperature is higher than 30° C., the amount of the compound of formula (2) is increased, and it is undesirable.

Note that it is preferred to carry out stirring for 1 minute to 10 hours after the completion of adding dropwisely. The time is more preferably 5 minutes to 5 hours, and even more preferably 10 minutes to 3 hours.

After the completion of the reaction, it is preferred to add an organic solvent thereto to extract bis(β-epoxypropyl)sulfide that is the sulfur-containing epoxy compound of interest. As the organic solvent, hydrocarbons, ethers, aliphatic hydrocarbons, aromatic hydrocarbons and halogenated hydrocarbons are preferred, and aromatic hydrocarbons and halogenated hydrocarbons are more preferred. Preferred specific examples thereof include toluene, benzene, xylene, dichloromethane and chloroform, and toluene is most preferred. Further, the obtained organic layer is preferably washed with water in order to remove the basic compound. Washing with water is carried out more preferably until the pH of water for washing becomes 10 or less, and even more preferably until the pH of water for washing becomes 9 or less.

The solvent is distilled away from the thus obtained organic layer, thereby obtaining bis(β-epoxypropyl)sulfide that is the sulfur-containing epoxy compound of interest.

According to the production method of the second preferred embodiment of the present invention, it is possible to produce a sulfur-containing epoxy compound in good yield in one step, wherein hydrogen sulfide is not used and the production of oligomer is suppressed, which was impossible by means of the conventional production methods. Since hydrogen sulfide is not used, the process is carried out in one step and the production of oligomer is suppressed, bis(β-epoxypropyl)sulfide that is the sulfur-containing epoxy compound can be easily obtained in good yield.

Third Preferred Embodiment

The third preferred embodiment of the present invention relates to a method for producing a sulfur-containing epoxy compound represented by formula (3) below (bis(β-epoxypropyl)polysulfide), wherein a metal polysulfide is reacted with an epihalohydrin.

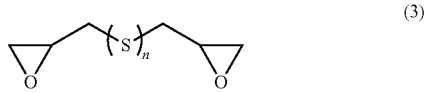

(3)

In the formula, n represents an integer of 2 or more.

Preferably, n is an integer from 2 to 5, and most preferably, n is 2.

The epihalohydrin to be used in the third preferred embodiment of the present invention includes every compound, but is preferably epichlorohydrin, which is easily available. The metal polysulfide to be used in the third preferred embodiment of the present invention includes every compound, but is preferably sodium polysulfide or potassium polysulfide, which is easily available, and more preferably sodium polysulfide. Sodium disulfide, sodium trisulfide, sodium tetrasulfide and sodium pentasulfide are even more preferred, and sodium disulfide is most preferred.

The reaction of the epihalohydrin with the metal polysulfide is as described below.

When reacting the epihalohydrin with the metal polysulfide, preferably, the metal polysulfide is added to the epihalohydrin to be reacted therewith. At this time, the metal polysulfide is preferably added in such a manner that the molar ratio of the epihalohydrin to the metal polysulfide becomes 5 to 20. The molar ratio is more preferably 5 to 15, and even more preferably 5 to 10.

When the molar ratio of the epihalohydrin to the metal polysulfide is less than 5, it causes reduction in the yield.

Meanwhile, when the molar ratio of the epihalohydrin to the metal polysulfide is more than 20, since a large excess amount of the epihalohydrin is used, it is economically undesirable.

The solvent is not particularly required to be used as long as the epihalohydrin reacts with the metal polysulfide, but it is preferred to use a solvent. When using a solvent, water, alcohols, ethers, aliphatic hydrocarbons, aromatic hydrocarbons and halogenated hydrocarbons are preferred, water and alcohols are more preferred, water and methanol are even more preferred, and water is most preferred. These solvents may be used solely or in combination.

It is preferred to use the solvent in order to dissolve the metal polysulfide. In addition, it is preferred to react the epihalohydrin with the metal polysulfide dissolved in the solvent, and it is more preferred to dropwisely add the metal polysulfide dissolved in the solvent to the epihalohydrin.

The reaction temperature is preferably −5 to 30° C., more preferably 0 to 20° C., and most preferably 5 to 15° C. When the reaction temperature is lower than −5° C., the reaction rate is reduced and it is economically undesirable. When the reaction temperature is higher than 30° C., the yield is reduced and it is undesirable.

Note that it is preferred to carry out stirring for 1 minute to 10 hours after the completion of the addition of the metal polysulfide in order to complete the reaction. The time is more preferably 5 minutes to 5 hours, and even more preferably 10 minutes to 3 hours.

After the epihalohydrin is reacted with the metal polysulfide, a basic compound may be further reacted therewith in order to complete the reaction.

The basic compound is not particularly limited and any basic compound may be used, but it is preferably amine, an alkali metal or an alkaline-earth metal salt, and more preferably an alkali metal or an alkaline-earth metal salt. Preferred specific examples thereof include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Among them, sodium hydroxide, potassium hydroxide, magnesium hydroxide and calcium hydroxide are preferred, and sodium hydroxide and potassium hydroxide are more preferred.

When adding the basic compound, any amount of the basic compound may be added, but in view of economic efficiency, the amount of the basic compound is 1 equivalent or less, and more preferably 0.5 equivalent or less relative to the metal polysulfide.

The solvent to be used at this time is not particularly limited, but water, alcohols, ethers, aliphatic hydrocarbons, aromatic hydrocarbons and halogenated hydrocarbons are preferred, water and alcohols are more preferred, water and methanol are even more preferred, and water is most preferred. These solvents may be used solely or in combination. Further, it is preferred to dissolve the basic compound in the solvent, followed by dropwisely adding it to the reaction product of the epihalohydrin and the metal polysulfide.

The reaction temperature is −5 to 30° C., preferably 0 to 20° C., and most preferably 5 to 15° C. When the reaction temperature is lower than −5° C., the reaction rate is reduced and it is economically undesirable. When the reaction temperature is higher than 30° C., the yield is reduced and it is undesirable.

Note that it is preferred to carry out stirring for 1 minute to 10 hours after the completion of adding dropwisely. The time is more preferably 5 minutes to 5 hours, and even more preferably 10 minutes to 3 hours.

After the completion of the reaction, it is preferred to add an organic solvent thereto to extract bis(β-epoxypropyl)polysulfide that is the sulfur-containing epoxy compound of interest. As the organic solvent, hydrocarbons, ethers, aliphatic hydrocarbons, aromatic hydrocarbons and halogenated hydrocarbons are preferred, and aromatic hydrocarbons and halogenated hydrocarbons are more preferred. Preferred specific examples thereof include toluene, benzene, xylene, dichloromethane and chloroform, and toluene is most preferred. Further, the obtained organic layer is preferably washed with water in order to remove the basic compound. Washing with water is carried out more preferably until the pH of water for washing becomes 10 or less, and even more preferably until the pH of water for washing becomes 9 or less. The solvent is distilled away from the thus obtained organic layer, thereby obtaining the sulfur-containing epoxy compound of interest.

According to the production method of the third preferred embodiment of the present invention, it is possible to produce bis(β-epoxypropyl)polysulfide that is an epoxy compound having polysulfide, wherein hydrogen sulfide is not used, which was impossible by means of the conventional production methods.

EXAMPLES

Hereinafter, the present invention will be specifically described by way of working examples, but the present invention is not limited thereto.

Example 1

A solution in which 40 g (0.5 mol) of 70% sodium hydrosulfide was dissolved in 100 ml of methanol was added dropwise to 232 g (2.5 mol) of epichlorohydrin (hereinafter abbreviated as EPCH) at 5 to 10° C. with stirring, and then the mixture was stirred for 1 hour. Next, a solution in which 70 g (1.75 mol) of sodium hydroxide was dissolved in 200 ml of water was added dropwise to the mixture at 5 to 10° C. with stirring, and then the mixture was stirred for 1 hour.

After the reaction was completed, extraction was carried out using 500 ml of toluene. After that, washing was carried out using 500 ml of water until the pH of water for washing became 9 or less, and the solvent was distilled away, thereby obtaining 63 g (yield: 86%) of bis(β-epoxypropyl)sulfide. Further, when the obtained bis(β-epoxypropyl)sulfide was analyzed by means of liquid chromatography, the compound of formula (2) was 4.8%. The results are shown in Table 1.

Example 2

The process was carried out in a manner similar to that in Example 1, except that the amount of EPCH was changed to 925 g (10 mol). The results are shown in Table 1.

Example 3

The process was carried out in a manner similar to that in Example 1, except that the amount of sodium hydroxide was changed to 20 g (0.5 mol). The results are shown in Table 1.

Example 4

The process was carried out in a manner similar to that in Example 1, except that the amount of EPCH was changed to 925 g (10 mol) and the amount of sodium hydroxide was changed to 20 g (0.5 mol). The results are shown in Table 1.

Example 5

The process was carried out in a manner similar to that in Example 1, except that the amount of EPCH was changed to 463 g (5 mol) and the amount of sodium hydroxide was changed to 40 g (1.0 mol). The results are shown in Table 1.

Comparative Example 1

The process was carried out in a manner similar to that in Example 1, except that the amount of EPCH was changed to 185 g (2 mol). Since the amount of EPCH was small, the yield was reduced, and the amount of the compound of formula (2) that is an impurity was increased. The results are shown in Table 1.

Comparative Example 2

The process was carried out in a manner similar to that in Example 1, except that the temperature during the time from the start of dripping of sodium hydrosulfide to the start of dripping of sodium hydroxide was set at 35° C. Since the reaction temperature was high, the yield was reduced, and the amount of the compound of formula (2) that is an impurity was increased. The results are shown in Table 1.

Comparative Example 3

The process was carried out in a manner similar to that in Example 1, except that the temperature during the time from the start of dripping of sodium hydrosulfide to the start of dripping of sodium hydroxide was set at −10° C. Since the reaction temperature was low, the yield was reduced. The results are shown in Table 1.

TABLE 1

| Examples | EPCH/NaSH (Molar ratio) | Reaction temperature 1 (° C.) | NaOH/NaSH (Molar ratio) | Reaction temperature 2 (° C.) | Yield (%) | Compound of formula (2) (%) |
|---|---|---|---|---|---|---|
| Example 1 | 5 | 5~10 | 3.5 | 5~10 | 86 | 4.8 |
| Example 2 | 20 | 5~10 | 3.5 | 5~10 | 91 | 1.8 |
| Example 3 | 5 | 5~10 | 1.0 | 5~10 | 82 | 3.4 |
| Example 4 | 20 | 5~10 | 1.0 | 5~10 | 85 | 1.4 |
| Example 5 | 10 | 5~10 | 2.0 | 5~10 | 89 | 2.4 |
| Comparative Example 1 | 4 | 5~10 | 3.5 | 5~10 | 68 | 10.5 |
| Comparative Example 2 | 5 | 35 | 3.5 | 5~10 | 56 | 15.5 |
| Comparative Example 3 | 5 | −10 | 3.5 | 5~10 | 25 | 0 |

Reaction temperature 1: temperature during the time from the start of dripping of sodium hydrosulfide to the start of dripping of sodium hydroxide
Reaction temperature 2: temperature during the time from the start of dripping of sodium hydroxide to the completion of the reaction

Example 6

250 ml of methanol was mixed with 232 g (2.5 mol) of epichlorohydrin (hereinafter abbreviated as EPCH) and the mixture was stirred to adjust the temperature to 10° C. A solution in which 120 g (0.5 mol) of sodium sulfide nonahydrate was dissolved in 1000 ml of water was added dropwise to the mixture with stirring at 5 to 10° C., and then the mixture was stirred for 1 hour. After the reaction was completed, extraction was carried out using 1000 ml of toluene. After that, washing was carried out using 500 ml of water until the pH of water for washing became 9 or less, and the solvent was distilled away, thereby obtaining 60 g (yield: 82%) of bis(β-epoxypropyl)sulfide. Further, when the obtained bis(β-epoxypropyl)sulfide was analyzed by means of liquid chromatography, the compound of formula (2) was 4.8%. The results are shown in Table 2.

Example 7

The process was carried out in a manner similar to that in Example 6, except that the amount of EPCH was changed to 925 g (10 mol). The results are shown in Table 2.

Example 8

The process was carried out in a manner similar to that in Example 6, except that the amount of EPCH was changed to 463 g (5 mol). The results are shown in Table 2.

Comparative Example 4

The process was carried out in a manner similar to that in Example 6, except that the amount of EPCH was changed to 185 g (2 mol). Since the amount of EPCH was small, the yield was reduced, and the amount of the compound of formula (2) that is an impurity was increased. The results are shown in Table 2.

Comparative Example 5

The process was carried out in a manner similar to that in Example 6, except that the reaction temperature was set at 35° C. Since the reaction temperature was high, the yield was reduced, and the amount of the compound of formula (2) that is an impurity was increased. The results are shown in Table 2.

Comparative Example 6

The process was carried out in a manner similar to that in Example 6, except that the reaction temperature was set at −10° C. Since the reaction temperature was low, the yield was reduced. The results are shown in Table 2.

TABLE 2

| Examples | EPCH/Na$_2$S (Molar ratio) | Reaction temperature (° C.) | Yield (%) | Compound of formula (2) (%) |
|---|---|---|---|---|
| Example 6 | 5 | 5~10 | 82 | 4.8 |
| Example 7 | 20 | 5~10 | 88 | 1.5 |
| Example 8 | 10 | 5~10 | 85 | 2.7 |
| Comparative Example 4 | 4 | 5~10 | 62 | 15.5 |
| Comparative Example 5 | 5 | 35 | 50 | 21.5 |
| Comparative Example 6 | 5 | −10 | 22 | 0 |

Example 9

250 ml of methanol was mixed with 232 g (2.5 mol) of epichlorohydrin and the mixture was stirred to adjust the temperature to 10° C. A solution in which 28 g (0.25 mol) of sodium disulfide was dissolved in 70 ml of water was added dropwise to the mixture with stirring at 5 to 10° C., and then the mixture was stirred for 2 hours. After the reaction was completed, extraction was carried out using 1000 ml of toluene. After that, washing was carried out using 500 ml of water until the pH of water for washing became 9 or less, and the solvent was distilled away, thereby obtaining 36 g (yield: 80%) of bis(β-epoxypropyl)disulfide. The results are shown in Table 3.

Example 10

The process was carried out in a manner similar to that in Example 9, except that the amount of EPCH was changed to 925 g (10 mol). The results are shown in Table 3.

Example 11

The process was carried out in a manner similar to that in Example 9, except that 0.25 mol of sodium trisulfide was used instead of sodium disulfide, thereby obtaining bis(β-epoxypropyl)trisulfide (yield: 62%). The results are shown in Table 3.

Example 12

The process was carried out in a manner similar to that in Example 11, except that the amount of EPCH was changed to 925 g (10 mol). The results are shown in Table 3.

Example 13

The process was carried out in a manner similar to that in Example 9, except that 0.25 mol of sodium tetrasulfide was used instead of sodium disulfide, thereby obtaining bis(β-epoxypropyl)tetrasulfide (yield: 51%). The results are shown in Table 3.

Example 14

The process was carried out in a manner similar to that in Example 13, except that the amount of EPCH was changed to 925 g (10 mol). The results are shown in Table 3.

Example 15

The process was carried out in a manner similar to that in Example 9, except that 0.25 mol of sodium pentasulfide was used instead of sodium disulfide, thereby obtaining bis(β-epoxypropyl)pentasulfide (yield: 35%). The results are shown in Table 3.

Example 16

The process was carried out in a manner similar to that in Example 15, except that the amount of EPCH was changed to 925 g (10 mol). The results are shown in Table 3.

Comparative Example 7

The process was carried out in a manner similar to that in Example 9, except that the amount of EPCH was changed to 185 g (2 mol). Since the amount of EPCH was small, the yield was reduced. The results are shown in Table 3.

Comparative Example 8

The process was carried out in a manner similar to that in Example 9, except that the reaction temperature was set at 35°

C. Since the reaction temperature was high, the yield was reduced. The results are shown in Table 3.

Comparative Example 9

The process was carried out in a manner similar to that in Example 9, except that the reaction temperature was set at −10° C. Since the reaction temperature was low, the yield was reduced. The results are shown in Table 3.

TABLE 3

| Examples | EPCH/metal polysulfide (Molar ratio) | Reaction temperature (° C.) | Yield (%) |
|---|---|---|---|
| Example 9 | 5 | 5~10 | 80 |
| Example 10 | 20 | 5~10 | 83 |
| Example 11 | 5 | 5~10 | 62 |
| Example 12 | 20 | 5~10 | 65 |
| Example 13 | 5 | 5~10 | 51 |
| Example 14 | 20 | 5~10 | 54 |
| Example 15 | 5 | 5~10 | 35 |
| Example 16 | 20 | 5~10 | 38 |
| Comparative Example 7 | 4 | 5~10 | 47 |
| Comparative Example 8 | 5 | 35 | 21 |
| Comparative Example 9 | 5 | −10 | 10 |

The invention claimed is:

1. A method for producing bis(β-epoxypropyl)sulfide or bis(β-epoxypropyl)polysulfide, which comprises adding a metal compound selected from the group consisting of a metal hydrosulfide, a metal sulfide and a metal polysulfide to an epihalohydrin at −5 to 30° C. in such a manner that the molar ratio of the epihalohydrin to the metal compound becomes 5 to 20 to thereby cause the reaction of the epihalohydrin with the metal compound.

2. The method according to claim 1, wherein the epihalohydrin is epichlorohydrin and the metal hydrosulfide is sodium hydrosulfide or potassium hydrosulfide.

3. The method according to claim 1, wherein the epihalohydrin is epichlorohydrin and the metal sulfide is sodium sulfide or potassium sulfide.

4. The method according to claim 1, wherein the epihalohydrin is epichlorohydrin and the metal polysulfide is sodium polysulfide or potassium polysulfide.

5. The method according to claim 1, wherein the metal hydrosulfide is added to the epihalohydrin at −5 to 30° C. in such a manner that the molar ratio of the epihalohydrin to the metal hydrosulfide becomes 5 to 20 to thereby cause the reaction of the epihalohydrin with the metal hydrosulfide; and then a basic compound is further added thereto in such a manner that the molar ratio of the basic compound to the metal hydrosulfide becomes 1.0 to 3.5 to thereby cause the reaction of the basic compound therewith at −5 to 30° C.

6. The method according to claim 2, wherein the metal hydrosulfide is added to the epihalohydrin at −5 to 30° C. in such a manner that the molar ratio of the epihalohydrin to the metal hydrosulfide becomes 5 to 20 to thereby cause the reaction of the epihalohydrin with the metal hydrosulfide; and then a basic compound is further added thereto in such a manner that the molar ratio of the basic compound to the metal hydrosulfide becomes 1.0 to 3.5 to thereby cause the reaction of the basic compound therewith at −5 to 30° C.

* * * * *